US007752926B2

(12) United States Patent
Caminade et al.

(10) Patent No.: US 7,752,926 B2
(45) Date of Patent: Jul. 13, 2010

(54) PRESSURE DETECTION AND MEASUREMENT SENSOR INCORPORATING AT LEAST ONE RESISTIVE FORCE-DETECTOR CELL

(75) Inventors: Jean-Luc Caminade, Saint Jean de Vedas (FR); Jean-Marie Basilio, Meze (FR); Olivier Coupard, Montpellier (FR)

(73) Assignee: Hill-Rom Industries, SA, Montpellier (FR)

( * ) Notice: Subject to any disclaimer, the term of this patent is extended or adjusted under 35 U.S.C. 154(b) by 0 days.

(21) Appl. No.: 12/199,869

(22) Filed: Aug. 28, 2008

(65) Prior Publication Data
US 2009/0056020 A1  Mar. 5, 2009

(30) Foreign Application Priority Data
Aug. 30, 2007 (FR) ................................. 07 57268

(51) Int. Cl.
*G01L 1/10* (2006.01)
(52) U.S. Cl. ................................ 73/862.625
(58) Field of Classification Search ............ 73/862.625, 73/780, 862.391; 177/210 C; 280/734, 735; 340/666, 667
See application file for complete search history.

(56) References Cited
U.S. PATENT DOCUMENTS

| 4,179,692 | A |   | 12/1979 | Vance |
|-----------|---|---|---------|-------|
| 4,186,734 | A | * | 2/1980  | Stratton ...................... 601/148 |
| 4,584,625 | A | * | 4/1986  | Kellogg ...................... 361/283.1 |
| 4,624,784 | A |   | 11/1986 | Lefebvre |
| 4,633,175 | A |   | 12/1986 | Ritchie et al. |
| 4,800,973 | A |   | 1/1989  | Angel |
| 4,814,661 | A |   | 3/1989  | Ratzlaff et al. |

(Continued)

FOREIGN PATENT DOCUMENTS
DE    30 11 266 A1    3/1980

(Continued)

OTHER PUBLICATIONS

State-of-the-Art Pointing Solutions for the OEM, FSR® Force Sensing Resistor® Integration Guide and Evaluation Parts Catalog, 400 Series Evaluation Parts with Suggested Electrical Interfaces, Versa Point Technology, Interlink Electronics, pp. 5-25, http://www.interlinkelectronics.com.

(Continued)

*Primary Examiner*—Lisa M Caputo
*Assistant Examiner*—Octavia Davis
(74) *Attorney, Agent, or Firm*—Barnes & Thornburg LLP

(57) ABSTRACT

The present disclosure relates to a pressure sensor, in particular for detecting and measuring at least one bearing pressure applied to a support device, in which said pressure sensor comprises at least one resistive force-detector cell placed between at least two protective plates suitable for avoiding any pressure bearing at a point or along a line directly against a surface of the resistive cell and for converting such a pressure into uniform pressure over the entire area of the resistive cell. The present disclosure also relates to a support device including such a pressure sensor and to a method of measuring pressures applied to such a support device by an object to be supported such as the body of a patient.

12 Claims, 3 Drawing Sheets

U.S. PATENT DOCUMENTS

| | | | |
|---|---|---|---|
| 5,253,656 A | | 10/1993 | Rincoe et al. |
| 5,353,012 A | | 10/1994 | Barham et al. |
| 5,515,044 A | | 5/1996 | Glatt |
| 5,564,144 A | * | 10/1996 | Weingartner et al. ... 297/452.27 |
| 5,808,552 A | | 9/1998 | Wiley et al. |
| 5,823,278 A | | 10/1998 | Geringer |
| 5,918,696 A | * | 7/1999 | VanVoorhies ............... 180/273 |
| 6,009,580 A | | 1/2000 | Caminade et al. |
| 6,067,019 A | | 5/2000 | Scott |
| 6,109,117 A | * | 8/2000 | Stanley et al. .......... 73/862.325 |
| 6,161,891 A | | 12/2000 | Blakesley |
| 6,169,138 B1 | * | 1/2001 | Petit et al. ................... 524/500 |
| 6,208,250 B1 | | 3/2001 | Dixon et al. |
| 6,289,749 B1 | * | 9/2001 | Sanders ................... 73/862.49 |
| 6,386,051 B1 | | 5/2002 | Yoshimi et al. |
| 6,404,106 B1 | * | 6/2002 | Dale et al. ................. 310/324 |
| 6,417,466 B2 | * | 7/2002 | Gross et al. ................. 177/211 |
| 7,296,312 B2 | | 11/2007 | Menkedick et al. |
| 7,409,735 B2 | * | 8/2008 | Kramer et al. ................. 5/713 |
| 7,459,645 B2 | * | 12/2008 | Skinner et al. .............. 177/144 |
| 7,464,605 B2 | | 12/2008 | Douglas et al. |
| 2002/0080037 A1 | | 6/2002 | Dixon et al. |
| 2003/0200611 A1 | | 10/2003 | Chaffee |
| 2006/0070456 A1 | | 4/2006 | Douglas et al. |

FOREIGN PATENT DOCUMENTS

| | | |
|---|---|---|
| EP | 1 821 088 A1 | 8/2007 |
| WO | WO 98/25112 | 6/1998 |

OTHER PUBLICATIONS

High Performance Foams, Rogers Corporation, pp. 1-2, http://www.rogers-corp.com/hpf/CT/Poron-l/aboutporon.htm, pp. 1-2, 2004.

FSR® Force Sensing Resistors®, Interlink Electronics.

Force Sensing Resistors, Frequently Asked Questions, Force Sensing Resistors from Interlink Electronics, FAQs, http://www.interlinkelec.com/support/faqs/page11.htm, p. 1, 2004.

European Search Report dated Jan. 23, 2009 for EP 08 16 3149.

* cited by examiner

PRESSURE DETECTION AND MEASUREMENT SENSOR INCORPORATING AT LEAST ONE RESISTIVE FORCE-DETECTOR CELL

The present application claims priority, under 35 U.S.C. §119(a), of French National Application No. 07 57268 which was filed Aug. 30, 2007 and which is hereby incorporated by reference herein.

BACKGROUND

The present disclosure relates to the field of pressure measurement, and relates more particularly to a pressure detection and measurement sensor including at least one resistive force-detector cell. The present disclosure further concerns, in particular, detecting and measuring pressures that are applied by the bodies of patients who are lying or sitting on healthcare support devices such as therapeutic mattresses, and in particular on support devices of the type comprising mattresses or cushions having inflatable cells, in order to regulate the inflation pressures of the cells of the support device so as to combat skin pathologies related to prolonged immobility on a bed or in a wheelchair, or in some other type of seat.

It is known, in medical practice, that interface pressures at the interfaces between patients' bodies and their support devices constitute the main factor in the development of skin complications, in particular, decubitus ulcers or "bedsores," due to the patients being immobile for prolonged periods on their beds or in their wheelchairs or seats.

One of the tried and tested techniques for combating formation and development of bedsores in patients consists in supporting the patients on beds that include mattresses having inflatable cells, the inflation pressures of the cells being regulated as a function of the morphology and of the weight of the patient so as to minimize the interface pressures between the patient's body and the surface of the mattress.

The interface pressures are evaluated or measured, in particular, by means of sensors that can be of various technologies and that are generally placed under the inflatable cells of the mattresses on which the patients are recumbent.

Depending on the technology implemented for them, such sensors make it possible to determine either the "float line," i.e. the distance to which the patient's body penetrates into the inflatable cells of the support device, or the pressures applied by the patient's body on the inflatable cells of the support device.

As a function of the response signal from the sensor, the penetration depth of or the pressure applied by the body on the support device is determined by an electronic control and regulation device and is compared with setpoint values that are predetermined as a function of the morphology of the patient. Whenever the depth or the pressure computed on the basis of the response signal from the sensor lies outside the range of setpoint values, the electronic control and regulation device actuates inflation means so as to adjust the inflation pressures of the inflatable cells of the support device so as to achieve support and comfort that are adapted to the morphology and to the position of the patient.

As indicated above, various sensors currently exist that have been specially developed to regulate inflation pressure of support devices having inflatable cells, such as therapeutic mattresses.

Mention can be made, in particular, of the Applicant's Documents FR-A-2 757 378 and WO-A-99 39 613 that describe respective sensors of distinct technologies.

Document FR-A-2 757 378 describes a support device having inflatable cells and provided with a control device including an inductive sensor placed under the inflatable cells of the mattress at the sacral zone of the patient. The inductive sensor makes it possible to measure a penetration distance of the body of a patient recumbent on the support device having the sensor, and to control means for inflating the cells so as to regulate the inflation pressures of the cells as a function of the penetration distance measured by the sensor.

A first drawback suffered by such an inductive sensor results from the high cost of manufacturing it, thereby having a considerable impact on the cost of the support device itself. Furthermore, such an inductive sensor has thickness of at least 5 centimeters (cm), which requires the support device incorporating it to have a large thickness, such a thickness making it more difficult to achieve safe coverage by the safety bars installed on the frame of the support device for the purpose of preventing falls.

Finally, it is necessary to ensure that such an inductive sensor satisfies the requirements of the standards relating to electromagnetic compatibility (EMC) because it is a sensor that generates an electromagnetic field.

Document WO-A-99 39 613 also presents a support device having inflatable cells for supporting the body of a patient. That support device is provided with a pressure sensor that itself includes an inflatable chamber inflated to a predetermined pressure. The sensor is received under the inflatable cells of the sacral zone for supporting the patient. Thus, the internal pressure of the inflatable chamber of the sensor varies with the pressure variations in the inflatable cells of the support device as a function of the morphology, of the weight, and of the movements of the patient on the support device. Electronic means then compare the respective pressures in the inflatable chamber of the sensor and in the inflatable cells of the support device and control the inflation means accordingly so as to regulate and adjust the inflation pressures inside the cells when the comparison of the pressures lies outside a predetermined range of setpoint values. In order to perform its sensing function, the sensor is filled with a fluid having low compressibility, e.g. silicone oil.

As with inductive sensors, a drawback with such a hydraulic (fluid-flow) sensor lies in the high cost of manufacturing it, thereby having a considerable impact on the cost of the support device itself. Furthermore, such a hydraulic sensor has thickness of at least 3 cm, which requires the support device incorporating it to have large thickness, such a thickness making it more difficult to achieve safe coverage by the safety bars installed on the frame of the support device for the purpose of preventing falls.

Finally, such a sensor having an inflatable chamber is heavy because it contains about 4 kilograms (kg) of silicone oil, which makes it difficult to handle.

The main problem with the various sensors and systems associated with regulating the inflation pressures of the cells of mattresses and of other support devices for therapeutic use is the cost of manufacturing them and of implementing them, that cost limiting use thereof to support devices that are used and operated in hospitals, in particular in departments specialized in care and treatment of patients having very reduced mobility and/or presenting high risks of developing bedsores.

In addition, sensors known from the prior art have their own structures that are generally complex, and they also require interfaces and electronic systems for making use of the measurements that are sophisticated, and that are not only expensive but also difficult to maintain, and difficult to alter or replace in the event of failure and/or of malfunction. It is then necessary to change the entire support device and not merely that element of the device that is defective, which is unpleasant for patients and particularly costly for hospitals.

Finally, the problem of the high cost of the sensors and systems for pressure regulation in existing support devices having inflatable cells currently rules out the use of such support devices for the vast majority of patients receiving healthcare treatment at home because public and private health insurance schemes generally refuse to pay or to reimburse the costs inherent to purchasing and using such support devices with inflatable cells.

There thus exists a major technical problem in designing and making a pressure sensor that is suitable for being used in support devices having inflatable cells, and in particular devices of the therapeutic mattress or therapeutic cushion type, in order to enable the pressures inside the cells to be regulated, and that has a cost very significantly lower than the costs of existing sensors and systems, while nevertheless procuring similar performance. Such a sensor is, in particular, desirable so as to reduce the costs of support devices and thus the costs of purchasing and of using them for home healthcare treatment.

A second technical problem also exists in making a sensor that is suitable for being used in support devices having inflatable cells in order to enable the pressures inside the cells to be regulated rapidly, and that is easy to replace in the event of failure or malfunctioning in systems for regulating existing support devices having inflatable cells.

Document U.S. Pat. No. 6,386,051 describes using a plurality of (in particular over 200) sensors having force sensitive resistors or FSR cells and organized into arrays over the entire top surface of a mattress, i.e. above the mattress, with a view to determining the posture of a patient on the mattress.

Document US-2006/0070456 also describes using a plurality of sensors (FSR sensors) applied to nearly the entire hard bed frame solely for the purpose of detecting the presence of a patient on the bed for alarm purposes.

It is also conventional to implement those types of FSR sensors in automobile seats. However, in that use too, the sole purpose is to detect whether or not the seat is occupied by a person, optionally while also determining the approximate weight of said person.

In the uses mentioned in those prior patents, the sensors are not required to deliver an analog signal with a sensitive and adapted response including a zone of signal linearity or proportionality as a function of the load exerted on the sensor. A logic (YES/NO) response is essentially all that is sought, i.e. contact or absence of contact on the sensor.

However, with the device disclosed herein, it is possible to enable the inflation of the cells of a mattress having inflatable cells and on which the patient is supported to be regulated as a function of the load detected by the sensor, and in particular by a single sensor located at a single zone of the mattress, in particular, in this example, the zone of the sacrum.

With the device disclosed herein, it should thus be possible, on the basis of the data relating to patient penetration into the mattress at that zone, as delivered by the sensor, in combination with the measurement of the internal pressure of the mattress, to deduce the penetration profile of the patient over the entire surface of the mattress.

In addition, with regard to the present disclosure, the sensor may be adapted to deliver responses that are usable, while also being placed under the mattress so as to avoid contact between the sensor and the patient, it being possible for such contact to cause bedsores, and, in particular, the sensor disclosed herein may be suitable for being placed between two mattress layers, under an upper layer made up of inflatable cells.

For this purpose, it is desired to provide a sensor that can give a response that is adapted in terms of sensitivity of an analog signal, having a zone of signal proportionality as a function of the load exerted on the sensor, for loads approximately in the range 40 kg to 210 kg (the weight of a person).

The impedance of an FSR varies as a function of the compression force per square centimeter ($cm^2$) exerted on it, but its response curve as a function of the applied force is generally non-linear. There therefore exist very large variations in resistance for low stresses, and, conversely, at higher stresses, resistance variations that are smaller. This makes it difficult to obtain an analog signal, i.e. a signal that is proportional to the load exerted.

SUMMARY

According to the present disclosure, a solution to these problems lies in a pressure sensor, in particular for detecting and measuring at least one bearing pressure applied against a support structure, in which said pressure sensor comprises at least one resistive force-detector cell applied against a rigid backing plate or soleplate, said backing plate being received in a recess formed in a first compressible intermediate layer, which recess is possibly a recess of shape complementary to the outline of said backing plate or soleplate, said first intermediate layer being placed between at least two protective plates. The two protective plates make it possible to avoid any pressure bearing at a point or along a line directly against a surface of said resistive cell and they contribute to converting such a pressure into a uniform pressure over the entire area of said resistive cell.

In some contemplated embodiments, the rigidity or semi-rigidity of the protective plates is such that they do not undergo any bending deformation under the effect of a load corresponding to the load of an adult weighing in the range 40 kg to 210 kg.

In one embodiment, the pressure sensor further comprises at least one second intermediate layer made of a compressible material, and disposed between one of said protective plates and said resistive cell, and in contact with said protective plate and with said resistive cell.

It can be understood that said second compressible intermediate layer is thus in contact with said resistive cell.

The pressure sensors disclosed herein are well adapted to detecting and measuring pressures and variations in pressures in a support device having inflatable cells. When the sensor is inserted under the inflatable cells of a support device, such as those in the prior art, with said rigid protective plates as top and bottom plates, the weight of the body of a patient recumbent on the inflatable cells of such a support device generates application of forces by the inflatable cells on the sensor, thereby causing the impedance of the resistive cells to vary inside the sensor, thereby in turn generating variation in the electrical signal measured across the terminals of the sensor.

The variations in the electrical signal across the terminals of the sensors disclosed herein are thus generally proportional to the movements of the patient's body on the inflatable cells of the support device and to the variations in fluid pressures in the inflatable cells consequent upon such movements. It is thus possible to use the electrical signal across the terminals of the sensor to control and regulate the inflation pressures of the cells of the support device, in particular by means of a control and regulation system for controlling and regulating the inflation pressures of cells of a support device such as an air mattress similar to the support device described by the Applicant in U.S. Pat. No. 6,009,580.

The illustrative sensor disclosed herein is also remarkable and particularly cost effective in that it comprises and uses resistive force-detector cells. Such resistive cell is a force sensitive resistor and one example of these is well known under the registered trademarks Force Sensing Resistors and/or "FSR." Such resistive cell or FSR is of an extremely simple structure, being constituted, in its simplest form, by two polymer sheets that are laminated together, one of the sheets being covered with an array of interdigitating electrodes made, for example, of copper or silver, and the other sheet being covered with a resistive material such as ink or with a semiconductive material, for example.

The relative simplicity of construction of such resistive cells or FSR's, which are mass-produced and in widespread use for a large number of varied applications, enables them to have costs that are particularly low compared with the costs of other electronic components, thereby enabling the pressure sensors disclosed herein to have a cost that is extremely low compared with the costs of sensors known from the prior art.

In addition, the structure of the sensors according to this is extremely simple and easy to replace or to repair in the event of sensor failure.

In addition, a resistive force-detector cell, which is an electronic component whose impedance decreases with increasing intensity of a force applied perpendicularly to its surface, is relatively insensitive to noise and to vibration, thereby making it easier to take measurements and to make use of them. Its wide range of impedance also makes it possible to use electronics with interfaces and of operation that are simpler than with other force sensors as presently known, such as extensometers and piezoelectric sensors, and the same applies to the electronic systems for operating pressure sensors or penetration measurement sensors hitherto used in support devices having inflatable cells, such as therapeutic mattresses and cushions.

In addition, since resistive force-detector cells are particularly thin (in the range 0.20 millimeters (mm) to 0.75 mm), and are insensitive to temperature, to chemicals and to humidity, these sensors are also much more robust and strong than prior art sensors, while also procuring precision and measurement fidelity at least as good as, if not better than, those procured with much more expensive known sensors. The impedance of the sensors disclosed herein varies linearly, following a curve of equation $Z\ (\Omega)=\alpha \times P$ (bars) over an impedance range from about 500 ohms ($\Omega$) to about 20 kilo-ohms (k$\Omega$).

The intermediate layers are said to be "compressible" in that they are compressible by pressure being applied against one or both of the two protective plates between which they are interposed.

It can thus be understood that said intermediate layers are less rigid than the protective plates.

As mentioned above, said resistive force-detector cell is pressed against a rigid backing plate between the two protective plates. Such a rigid backing plate is particularly suitable for avoiding any deformation of the resistive cells of the sensor when said sensor is put in place under the inflatable cells of a support device. Such deformation of the resistive cells should be avoided because it would give rise to impedance variations in the resistive cells that are not due to the forces that are to be measured by the sensor, i.e. the forces related to the movements of the body of a patient recumbent on the inflatable cells of a support device. It is therefore possible to use rigid soleplates for the resistive cells of the sensors in order to prevent such deformation of the resistive cells.

More particularly, each said resistive cell is received in a recess formed in a compressible intermediate layer disposed between the protective plates. This characteristic makes it possible to protect the resistive cells and to reduce the sensitivity of the sensor so that the measurements taken do indeed correspond to pressure forces that are large and that are representative of movements of a patient recumbent on a support device having inflatable cells.

The first intermediate layer that is provided with recesses or cutouts in which the backing plates and resistive cells are received serves to accommodate the thickness of the resistive cell over the entire area of the protective plates and also, where applicable, forms spacers between the various resistive cells when a plurality of said resistive cells are received in a plurality of recesses.

The two intermediate layers of compressible material damp the pressure forces applied to the sensor and sensed by the resistive cells, and they thus contribute to making the pressure forces applied to the surface more uniform at the surface(s) of the resistive cells so as to adapt the sensitivity and the linearity of the response signal from the resistive cell as a function of the forces applied.

The two protective plates make it possible to avoid any pressure bearing at a point or along a line directly against a surface of said resistive force-detector cell, and they also contribute to converting such pressure into uniform pressure over the entire area of said resistive cell.

In accordance with this disclosure, this sensor configuration makes it possible to adjust the dynamic range of the signal as a function of the materials chosen and of the dimensioning thereof, in particular in terms of thickness.

These intermediate layers are dimensioned to make it possible to obtain a sensor response that is substantially linear in a load range corresponding to the weight of person from 40 kg to 210 kg.

More particularly, said protective plates are made of a rigid material, and in particular of a metal or synthetic material. In a variant, and also according to this disclosure, the protective plates may also be made of an expanded synthetic material, which, although it is expanded, is of density imparting a certain amount of rigidity or of semi-rigidity.

In some embodiments, the intermediate layer is formed of at least one compressible material suitable for undergoing a reduction in thickness of not more than 40% under a pressure lying in the range 100 Newtons per square centimeter (N/cm$^2$) to 250 N/cm$^2$.

It is thought that, in order to obtain a linear response that is reliable and reproducible from the sensor, the maximum flattening of the compressible layer of the sensor should be about 40%.

In some embodiments of the sensor contemplated herein, the intermediate layer is made of a synthetic material foam, such as a polyurethane foam, and is of a thickness lying in the range of about 3 mm to about 30 mm.

In such embodiments, the foam of the intermediate layers has density in the range of about 35 kilograms per cubic meter (kg/m$^3$) to about 65 kg/m$^3$.

The thickness of the intermediate layer can, in particular, vary depending on the use, and can even be greater than 30 mm in certain situations.

In other embodiments, the intermediate layer is made of a composite material that is woven and/or structured in three dimensions, in particular a composite material composed of woven polyester. One example of such three-dimensionally woven composite materials are, in particular, manufactured and sold by John Heathcoat & Co. Ltd., a company registered in the United Kingdom.

According to another embodiment, the rigid backing plate of at least said resistive cell is constituted by a metal plate, in particular based on aluminum, or else, in a variant, by a plate of resin, in particular of epoxy resin.

In still another embodiment, said resistive cell is constituted by a printed circuit on a rigid plate, constituting said soleplate, and in some instances on a plate of epoxy resin. This particular embodiment of the a resistive force-detector cell constitutes a high level of integration and of compactness contemplated for the sensor of the present disclosure, even though it is more costly to make.

Also according to embodiments contemplated herein, it is also possible for the sensor to comprise a plurality of resistive cells that can be placed in an array and uniformly distributed between said protective plates, while being connected together in series or in parallel. In these embodiments, not only is the detection and measurement precision of the sensor increased but also, if so desired, the detection and measurement area is increased, thereby increasing the capability of the measuring to withstand interfering distortion.

This disclosure also contemplates a support device, in particular a mattress or a cushion, for supporting an element to be supported, in particular the body of a patient, said device comprising at least one upper layer resting on at least one lower layer for supporting said upper layer, said upper and lower layers being, in some embodiments, encased in a preferably removable cover. The contemplated support device is characterized by the fact that it further comprises a pressure sensor as discussed above, which sensor is placed between the upper layer and the lower layer and is connected to a control and regulation device for detecting the pressures applied by the element to be supported on said upper layer of the support device and for determining the values of said pressures and the locations thereof.

In one embodiment of such a support device, the upper layer is made up of cells that are inflatable with a fluid, in particular air, and said cells communicate fluidly with one another and with inflation means suitable for being operated by said control device for the purpose of filling or of emptying the inflatable cells of said upper layer of the mattress, as a function of the pressures detected and measured by the sensor on said upper layer.

In another embodiment of a support device according to this disclosure, the lower layer is also made up of cells that are inflatable with a fluid, in particular air, and that communicate with said inflation means connected to and suitable for being operated by said control device for the purpose of filling or emptying said cells of the lower layer, as a function of the pressures detected and measured by said sensor and/or of the inflation pressures of the cells of the upper layer of the support device.

In still another embodiment of a support device according to this disclosure, the upper layer and the lower layer communicate fluidly, such as pneumatically, with each other in a manner such that they are at substantially the same pressure.

Finally, the present disclosure also contemplates a method of measuring pressures applied to a support device, in particular a mattress or a cushion, by an object to be supported, in particular the body of a patient, in which method said pressures applied by the object to be supported on the support device are detected and measured and located by means of a sensor comprising at least one resistive force-detector cell, said sensor being placed in said support device or under said support device.

In this method, said support device comprises cells inflatable with a fluid, in particular air, fluidly communicating with one another and with inflation means for inflating said cells, which means are operated by a control device that is connected electrically to the pressure sensor in such a manner as to inflate or deflate said inflatable cells of the support device, as a function of the pressures detected and measured by said sensor.

This method is particularly useful in that it makes it possible, inter alia, to regulate the inflation pressures of air cells of a support device such as a therapeutic mattress as a function of impedance variations in the resistive force-detector cells, which variations are both very simple to detect and measure, and also very simple to use.

In addition, since the various sensors disclosed herein are also sensitive to lateral movement forces, it also makes it possible, when they are associated with a suitable control and regulation device, to monitor the movements of a patient on the inflatable mattress and to analyze in three dimensions the position of a patient on the inflatable cells of the mattress so as to adjust the inflation pressures of the cells accordingly.

BRIEF DESCRIPTION OF THE DRAWINGS

Other characteristics and features appear from the following detailed description of variant embodiments of the support devices of the present disclosure, given with reference to the accompanying drawings, in which.

DETAILED DESCRIPTION

Figure 1A:
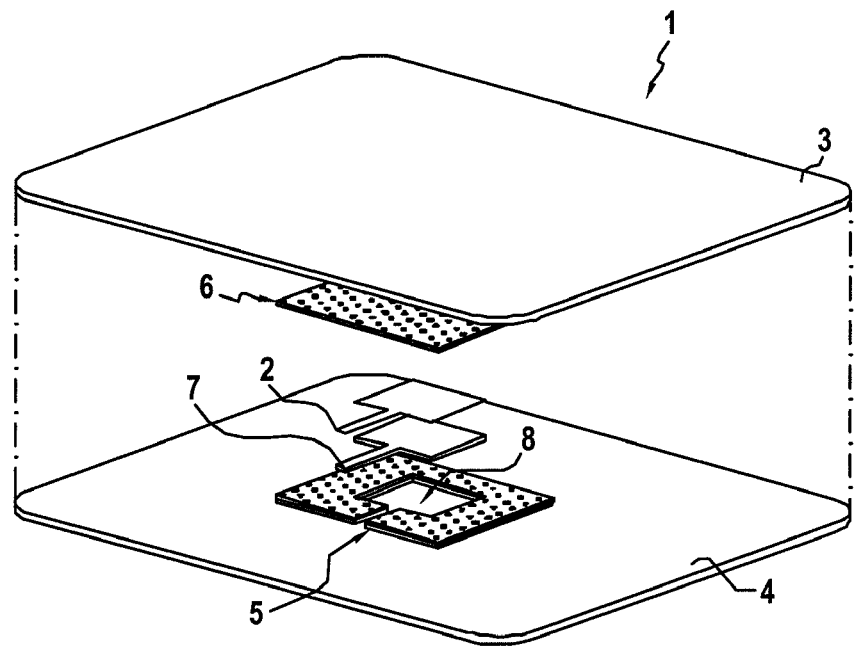
FIG. 1A is a diagrammatic exploded perspective view of a first embodiment of a pressure sensor according to this disclosure.

FIG. 1A shows a pressure sensor according to this disclosure designated by the overall reference 1 in one contemplated embodiment.

The sensor 1 firstly includes a resistive force-detector cell 2 referred to in the remainder of the description as an "FSR cell." Such FSR cells, in particular produced and sold, for example, by Force Imaging Technologies, Inc., are well known to the person skilled in the art, and, for this reason, are not described in any further detail in the present description.

The FSR cell 2 is sandwiched between two rigid or semi-rigid protective plates 3, 4. The protective plates for protecting the FSR cell 2 can, in particular, be made of a thermoplastic material such as polyvinyl chloride (PVC), polypropylene (PP), Polyethylene (PE), or indeed Acrylonitrile Butadiene Styrene (ABS).

In a variant, the plates 3, 4 for protecting the FSR cell 2 of the sensor 1 can also be made of metal, in particular, of aluminum, for example.

The FSR cell 2 is also pressed, e.g. by being stuck by adhesive bonding, against a rigid backing plate 7, constituted, for example, of a plate made of aluminum or of epoxy resin and received in a recess 8 formed in a layer 5 of absorbent and compressible material stuck to the stiffener plate 4 by adhesive bonding.

A second layer 6 of absorbent and compressible material is also stuck to the inside face of the plate 3 by adhesive bonding.

The rigid backing plate 7 of the FSR cell 2 represents a reference surface for pressure-force measurement by the sensor. The FSR cell 2 is sensitive to the slightest compression at a point and thus to interference compression and other twisting or bending due to the backing plate against which it or the sensor itself is applied having a poor surface state. It is thus preferable to procure a soleplate for the FSR cell that smoothes out and accommodates any defects in the surface on which the sensor is located in order to perform the pressure measurements.

In the same manner and for the same reasons, the layers 5, 6 form interface layers between the FSR cell and the protective plates 3, 4. The layers 5, 6 can, in particular, be made of synthetic foam (e.g. polyurethane or polyethylene) or of a three-dimensionally woven synthetic material, in particular three-dimensionally woven polyester such as the material Spacetec® manufactured and sold by John Heathcoat & Co. Ltd., registered in the United Kingdom.

Said layers 5, 6 also perform the function of making the space between the protective plates 3 and 4 denser, firstly so as to damp the pressure forces applied to the sensor 1 and sensed by the FSR cell 2, and secondly so as to reduce the intensity of the pressure forces sensed by the FSR cell 2 and so as to make the distribution of the pressure forces applied to the sensor at the surface of the FSR cell 2 more uniform in order to improve the sensitivity and the linearity of the response signal from the FSR cell 2 as a function of the applied forces.

The impedance of the FSR cell 2 varies as a function of the compression force per square centimeter that is exerted on it, and its response curve as a function of applied force is non-linear. There therefore exist very large variations in resistance for small stresses, and, conversely, at higher stresses, the variations in resistance are smaller.

According to this disclosure, the layers 5, 6 are, in particular, dimensioned to obtain a substantially linear response from the sensor within a range of pressures applied to a support device having inflatable cells by the bodies of people having weights in the range 40 kg to 210 kg.

Thus, the sensor 1 discloses herein is a composite laminate made up of an FSR cell 2 applied against a soleplate 7, encapsulated by two intermediate layers 5, 6 of absorbent and compressible materials between two rigid or semi-rigid protective plates 3, 4 that are, in some embodiments, secured together by suitable reversible coupling means.

In addition, the types and the characteristics of the FSR cello 2 and of the component materials of the protective plates 3, 4 and of the intermediate layers 5, 6 are chosen so that the response signal from the sensor 1 is substantially proportional to the pressure forces that the sensor is designed to be capable of detecting and measuring as a function of the use that is to be made of it. In particular, when it is used for regulating the inflation pressures of inflatable cells of a healthcare support device such as a therapeutic mattress, the sensor 1 is designed so as to provide a response signal that is substantially proportional to the weights of the patients.

Figure 1B:
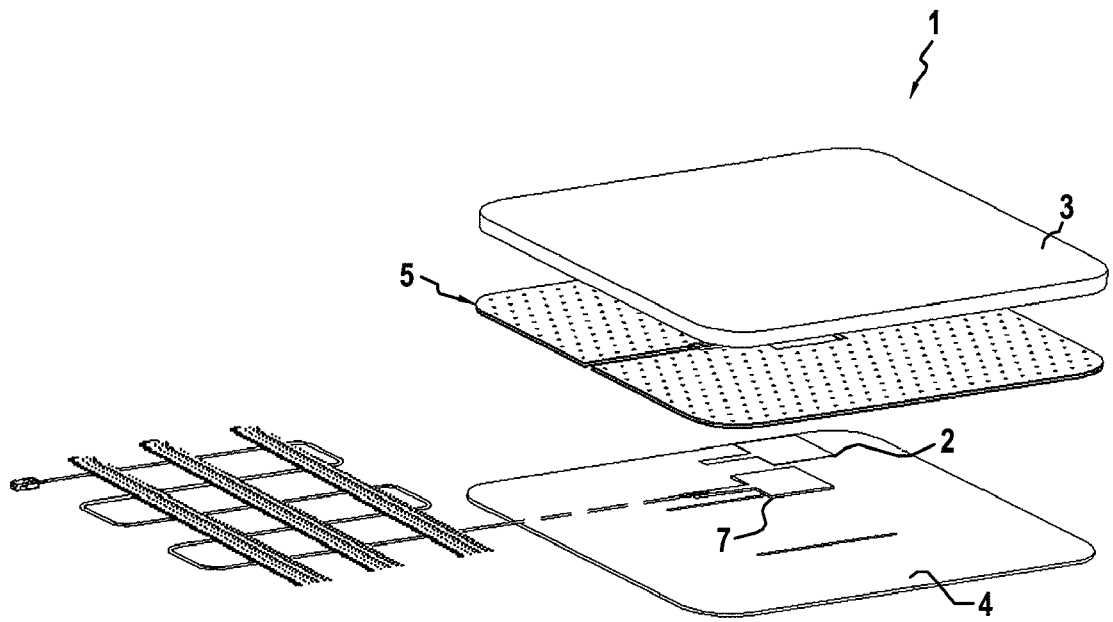
FIG. 1B is a diagrammatic exploded perspective view of a second embodiment of a pressure sensor according to this disclosure.

FIG. 1B shows a variant embodiment of the sensor 1 of FIG. 1A, in which variant embodiment the two intermediate layers 5, 6 are replaced with a single intermediate layer 5 of format substantially identical to the format of the protective plates 3, 4, and of thickness substantially equal to the total thickness of the two layers 5, 6, in the embodiment of FIG. 1A or slightly smaller than said total thickness. The FSR cell 2 and its soleplate 7 are then received in a recess of complementary shape formed by being cut out from the intermediate layer 5.

Figure 2:
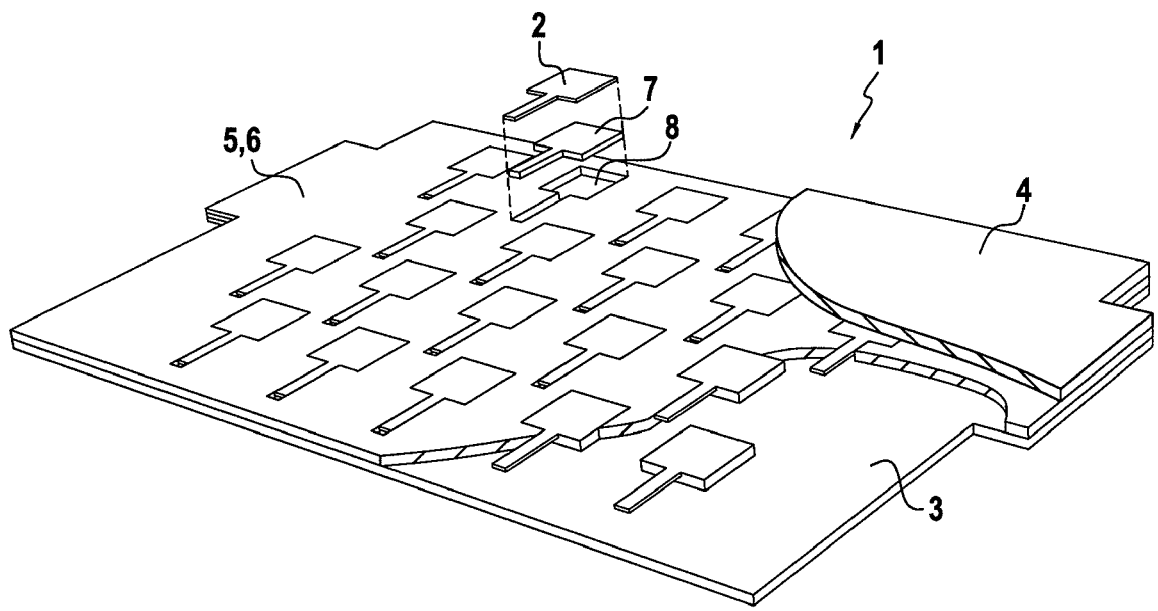
FIG. 2 is a view in perspective and partially in section showing a third embodiment of a pressure sensor of this disclosure.

FIG. 2 shows a third embodiment of the pressure sensor 1 according to this disclosure. In this figure, the elements that are of construction and of function similar to or identical to those of the elements of the sensor of FIGS. 1A and 1B bear like reference numerals.

In the embodiment of FIG. 2, the sensor 1 comprises a plurality of FSR cells 2. The FSR cells 2, the number of which can vary in the range 1 to 25, typically as a function of the area of the sensor 1 that is to be obtained, are stuck by adhesive bonding to respective rigid backing plates or soleplates 7, e.g. an aluminum or epoxy resin plate, and are placed evenly and uniformly in staggered manner in recesses 8 of shape complementary to the outline of each of the FSR cells 2 and of the backing plate 7 thereof.

The second intermediate layer of compressible material 6 is applied on the FSR side and not on the rigid soleplate side, and is in contact with the FSR cell.

The thickness of the first intermediate layer 5, and thus the thickness of the recesses 8 is substantially identical to the cumulative thickness of the FSR cells 2 and of the rigid soleplates.

The recesses 8 for receiving the FSR cells 2 are formed by cutouts in an intermediate layer 5, e.g. a synthetic foam or a three-dimensionally woven synthetic material, in particular three-dimensionally woven polyester such as Spacetec® manufactured and sold by John Heathcoat & Co. Ltd., a company registered in the United Kingdom.

Figure 3:
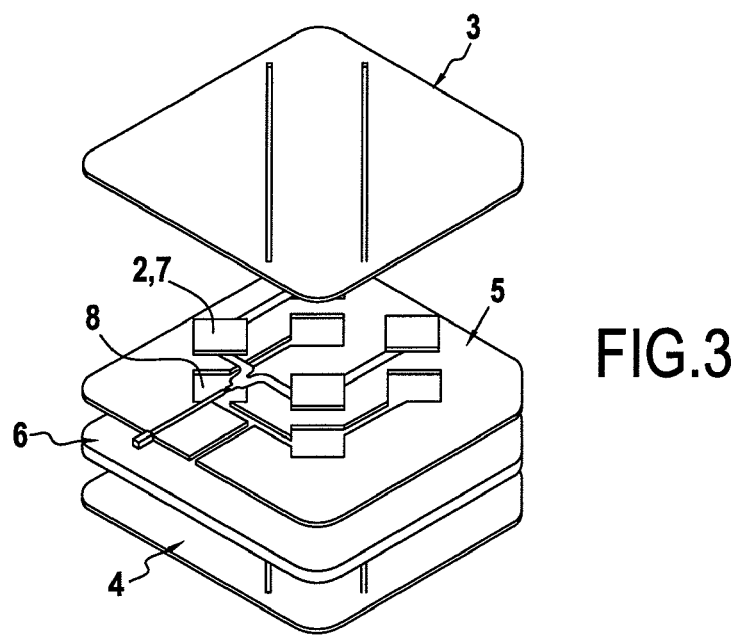
FIG. 3 is a view showing an embodiment of a sensor with four resistive cells placed in a square configuration.

In FIGS. 1A and 3, when the intermediate layers are made of synthetic foam, the first intermediate layer 5 is in some instances a foam that is denser, in particular with a density of 65 kg/m$^3$, and thinner than the foam of the second intermediate layer 6 whose density is, for example, 35 kg/m$^3$, the thickness of the first and second intermediate layers being in a ratio of 4 to 10, for example.

The intermediate layer 5 thus forms spacers between the FSR cells 2, whose thickness is chosen as a function of the sensitivity and of the precision that is desired for the sensor, said intermediate layer 5 replacing, at least in part, the two intermediate layers 5, 6 of the sensor of FIG. 1A.

The intermediate layer 5 is itself stuck to a first protective plate 4 by adhesive bonding, and covered with a second protective plate 3, both of which plates are made of synthetic foam, and possibly of polyethylene foam.

The sensor 1 shown in FIG. 2 and that is referred to below as a "multi-cells" sensor, is particularly adaptable in that the presence of spacers between each FSR cell 2 makes it possible to modify the response of the sensor 1 to the pressure stresses that are applied to it and that it senses. This possibility enables the dynamic range of the response to be adjusted substantially exactly as a function of the densities of the materials used for making the protective plates 3, 4 or the spacers 5 of the sensor 1.

The multi-cells sensor makes it possible to increase the read area and the read precision, and, also, when the sensor is a pressure sensor giving a three-dimensional response as mentioned below, it makes it possible to determine with more precision the position of the patient in the mattress.

In the embodiment shown in FIG. 2, the sensor 1 can be configured so as to deliver as many output signals as there are FSR cells 2, or else a single signal. In the former situation, the sensor 1 then has a connection port (not shown) at which the connection terminals of each of the FSR cells 2 are grouped together.

In the latter situation, the FSR cells 2 of the sensors are then connected together in series or in parallel, so as to form a closed measurement circuit having two single terminals across which the output signal from the sensor can be measured.

In addition, in this embodiment, it is also possible to connect the FSR cells 2 of the senor in a manner such as to perform measurements in three dimensions in order to measure not only the intensity of the pressure forces applied to the sensor but also their application position on the sensor 1.

By reading each FSR cell individually, it is possible to determine which FSR cell of the sensor is undergoing the stress. Thus, when such a sensor is being used for pressure detection in a therapeutic support device, in particular a device having inflatable cells, it is then possible to detect the location of the patient on the support device by detecting the pressure applied by the patient's body and the location of that pressure by means of the sensors of the present disclosure. In some of the prior art devices, a patient falling out of bed is detected only once the patient has fallen. With the devices disclosed herein, it is possible to prevent the fall because it is possible to detect when the patient is on the edge of the mattress. This also makes it possible to detect whether the patient is restless.

The pressure sensors 1 of the present disclosure, as presented above with reference to FIGS. 1 and 3, has been developed, in particular, for use in regulating the inflation pressures of inflatable cells of support devices such as therapeutic mattresses or cushions, as is described below with reference to FIG. 4 that shows a support device 10 having inflatable cells, of the therapeutic mattress type.

The support device 10 makes it possible to support an element to be supported, in particular the body of a patient such as a human patient.

Said support device comprises an inflatable mattress 11 made up of at least one closed or controlled-release inflatable cell.

Figure 4:
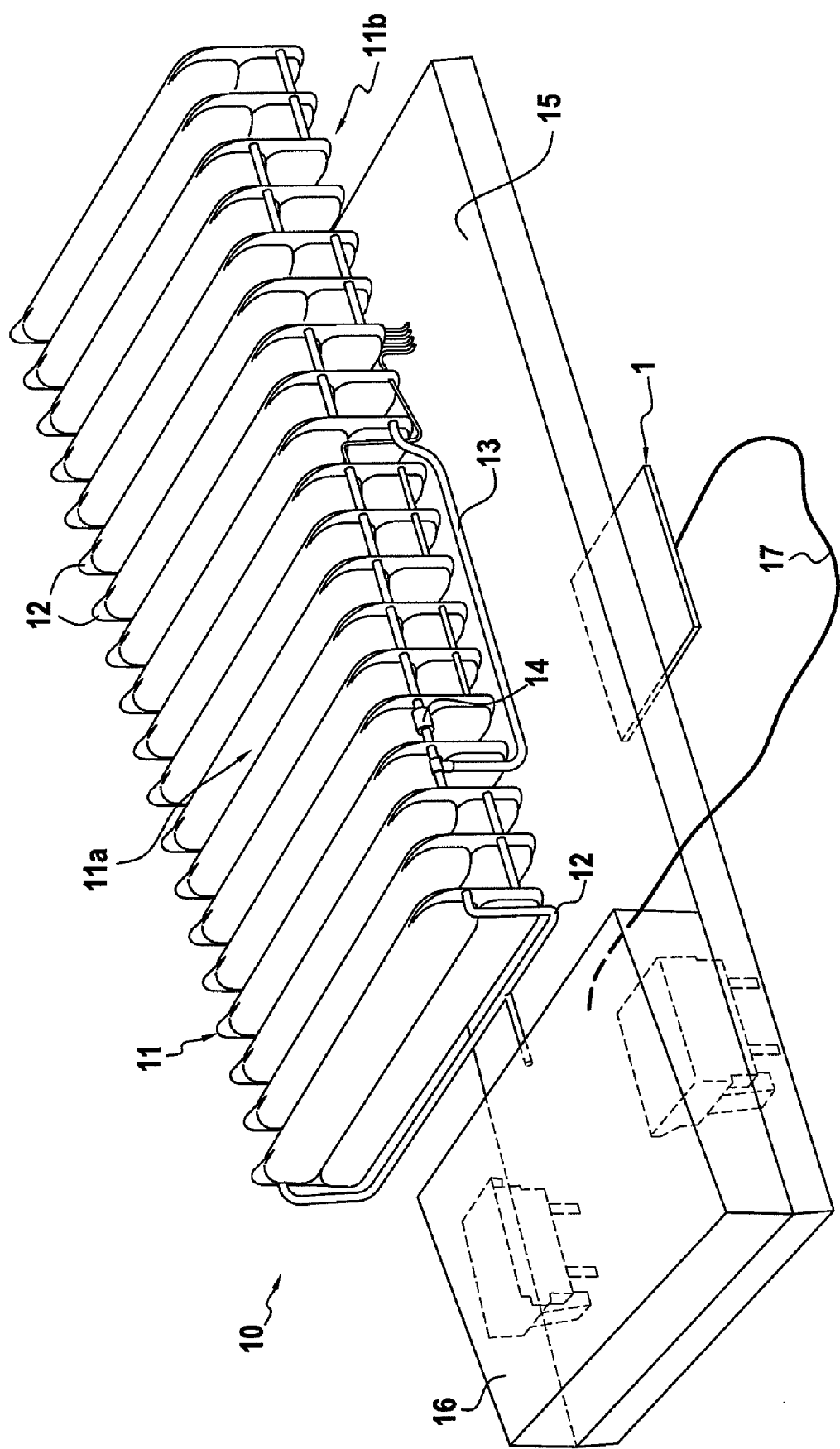
FIG. 4 is an exploded perspective view of a support device including a pressure sensor according to this disclosure.

In some embodiments, such as shown in FIG. 4, the mattress 11 is made up of a multiplicity of inflatable cells 12 that communicate with one another via pipes 13 and valves 14 for fluid, such as pneumatic, connection.

The inflatable cells 12 can be of any type known to the person skilled in the art and, in particular, designed by flat butt welding (heat sealing) together two flexible sheets of polyurethane (PUR) or of any other suitable thermoplastic material.

The inflatable mattress 11 has a top face 11a serving to receive an element to be supported such as the body of a patient and a bottom face 11b resting on a lower layer forming a reference surface 15, generally constituted by a mattress of cellular material such as high-density foam which, itself, can rest directly or indirectly on a bed base (not shown). In a variant, said lower layer 15 can also be made up of inflatable cells containing a fluid, in particular air.

The support device 10 further comprises a foot section 16 having a control and regulation device for controlling and regulating the filling pressures of the inflatable cells 12 of the mattress 11 (and, where applicable, of the inflatable cells of the reference lower surface 15).

The foot section 16 having the control and regulation device is, illustratively, placed in alignment with the rest of the mattress 11 at one end thereof, on the lower layer 15. The control and regulation device comprises, in particular, means for filling the cells 12 of the mattress 11, which means comprise a compressor and/or a pump connected via the pipes 13 and valves 14 to the cells 12 in order to fill them with a filling fluid, in particular air, or to empty them of said fluid.

The control and regulation device 16 also includes electronic means (not shown) for operating filling means that are servo-controlled to pressure measurement means.

The pressure measurement means are essentially of two types, namely firstly means (not shown) for measuring the inflation pressures of the cells 12, in particular in-line pressure measurement means mounted in series in the fluid connection pipes of the cells, and secondly a pressure sensor 1 of the type contemplated herein in a form similar to the form described above with reference to FIG. 1 or to FIG. 2.

The pressure sensor 1 is, in various embodiments, received under the bottom surface 11b of the mattress 11 or under the reference surface 15, and it is connected via an electrical connection 17 to the control and regulation device 16.

The set comprising the upper layer 11 and the lower layer 15, the control and regulation device, the pipes 13 and valves 14, and the sensor 1 is typically encased in a protective cover that, in some instances, is also removable in order to give easy access to the elements of the support device and also in order to make easy replacement or cleaning possible whenever desired.

When the patient is positioned on the mattress, the sensor 1 undergoes compression stress and its impedance varies proportionally to the weight of the patient relative to the body area of said patient ($kg/cm^2$). The impedance variation takes account of the morphology of the patient because the information is different, for example, for two people who have the same weight but not the same pelvis widths and who do have the same penetration into the mattress and therefore do not have the same regulation pressures.

This resistance variation is taken into account in the control and regulation device which modifies its regulation setpoint proportionally to the resistance variation. A comparator of the control and regulation device compares the pressures in the cells 12 by means of a pressure sensor with the new setpoint. If the pressure is too high relative to the new setpoint, the control and regulation device opens its deflation solenoid valve. If the pressure is too low relative to the new setpoint, the control and regulation device initiates startup of its inflation system. In general, a single sensor 1 is placed under the zone for supporting the sacrum, and it is possible to deduce therefrom the pressures at the other zones of the body of the patient recumbent on the support device insofar as 80% of people have a similar mass/volume distribution of the various portions of the body.

For people outside this average or in order to obtain an even more specific response, a plurality of sensors 1 can then installed under the various portions of the body in the support device.

The sensor of FIG. 1A is placed with the protective plate 3 that is applied against the second intermediate layer 6 being the top plate.

Similar results are obtained when the protective plate 4 applied against the first intermediate layer 5 is the top plate, as shown in FIG. 3.

The invention claimed is:

1. A pressure sensor, in particular for detecting and measuring at least one bearing pressure applied against a support device, wherein said pressure sensor comprises at least one resistive force-detector cell applied against a rigid backing plate, said backing plate being received inside a recess formed in a first compressible intermediate layer, which recess has a shape complementary to the outline of an outer edge of said backing plate, said first intermediate layer being placed between at least two rigid or semi-rigid protective plates, wherein said protective plates are made of a metal or synthetic rigid material.

2. The pressure sensor according to claim 1, further comprising at least one second intermediate layer made of a compressible material, and disposed between one of said protective plates and said resistive cell, and in contact with said protective plate and with said resistive cell.

3. The pressure sensor according to claim 1, wherein said protective plates are made of a plastics material chosen from PVC, PP, PE, or ABS.

4. The pressure sensor according to claim 1 or 2, wherein said intermediate layer is formed of at least one compressible material suitable for undergoing a reduction in thickness of 40% under a pressure lying in the range 100 N/cm² to 250 N/cm².

5. The pressure sensor according to claim 1 or 2, wherein said intermediate layer is made of a cellular material, and preferably of a polyurethane foam, and is of a thickness lying in the range 3 mm to 30 mm.

6. The pressure sensor according to claim 1 or 2, wherein said intermediate layer comprises a material structured in three dimensions, preferably a material based on woven polyester.

7. The pressure sensor according to claim 1, wherein said rigid backing plate of at least said resistive cell is constituted by a metal plate, in particular based on aluminum.

8. The pressure sensor according to claim 1, wherein said rigid backing plate of at least said resistive cell is constituted by a plate of resin, in particular of epoxy resin.

9. The sensor according to claim 1, comprising a plurality of said resistive cells.

10. A pressure sensor, in particular for detecting and measuring at least one bearing pressure applied against a support device, wherein said pressure sensor comprises at least one resistive force-detector cell applied against a rigid backing plate, said backing plate being received inside a recess formed in a first compressible intermediate layer, which recess has a shape complementary to the outline of an outer edge of said backing plate, said first intermediate layer being placed between at least two rigid or semi-rigid protective plates, wherein said protective plates are made of an expanded or cellular synthetic material.

11. A pressure sensor, in particular for detecting and measuring at least one bearing pressure applied against a support device, wherein said pressure sensor comprises at least one resistive force-detector cell applied against a rigid backing plate, said backing plate being received inside a recess formed in a first compressible intermediate layer, which recess has a shape complementary to the outline of an outer edge of said backing plate, said first intermediate layer being placed between at least two rigid or semi-rigid protective plates, wherein, at least, said resistive cell is constituted by a printed circuit on a rigid plate, in particular on a plate of epoxy resin.

12. A pressure sensor, in particular for detecting and measuring at least one bearing pressure applied against a support device, wherein said pressure sensor comprises at least one resistive force-detector cell applied against a rigid backing plate, said backing plate being received inside a recess formed in a first compressible intermediate layer, which recess has a shape complementary to the outline of an outer edge of said backing plate, said first intermediate layer being placed between at least two rigid or semi-rigid protective plates, wherein the at least one resistive force-detector cell comprises a plurality of said resistive cells, the plurality of said resistive cells being placed in an array and uniformly distributed between said protective plates, in a plurality of said recesses in a said intermediate layer, said resistive cells being connected together in series or in parallel.

* * * * *